United States Patent
Ogueli et al.

(10) Patent No.: US 9,638,354 B1
(45) Date of Patent: May 2, 2017

(54) CABLE ORGANIZING ASSEMBLY

(71) Applicants: Vivian Ogueli, Bellflower, CA (US); Godwin Ogueli, Bellflower, CA (US)

(72) Inventors: Vivian Ogueli, Bellflower, CA (US); Godwin Ogueli, Bellflower, CA (US)

( * ) Notice: Subject to any disclaimer, the term of this patent is extended or adjusted under 35 U.S.C. 154(b) by 0 days.

(21) Appl. No.: 15/002,680

(22) Filed: Jan. 21, 2016

(51) Int. Cl.
| | |
|---|---|
| *A61M 5/32* | (2006.01) |
| *F16L 3/223* | (2006.01) |
| *F16L 3/10* | (2006.01) |
| *F16B 47/00* | (2006.01) |
| *A61G 7/05* | (2006.01) |
| *A61M 5/14* | (2006.01) |

(52) U.S. Cl.
CPC .......... *F16L 3/2235* (2013.01); *A61G 7/05* (2013.01); *A61M 5/1418* (2013.01); *F16B 47/003* (2013.01); *F16L 3/1041* (2013.01); *F16L 3/1075* (2013.01)

(58) Field of Classification Search
CPC ..... F16L 3/2235; F16L 3/1041; F16L 3/1075; F16L 47/003; A61G 7/05; A61G 7/1076; A61M 5/1418; A61M 25/02; A61M 25/024; A61M 2025/024
USPC ........ 248/68.1; 128/346, 849, 885; 604/180, 604/174
See application file for complete search history.

(56) References Cited

U.S. PATENT DOCUMENTS

| | | | |
|---|---|---|---|
| 4,896,465 A * | 1/1990 | Rhodes | A61M 5/1418 128/849 |
| 5,127,545 A * | 7/1992 | French | A45F 5/00 221/102 |
| D328,820 S | 8/1992 | Davie | |
| 5,558,440 A * | 9/1996 | Miller | A45C 1/04 224/219 |
| 7,255,251 B1 | 8/2007 | Smith | |
| 2004/0118982 A1 | 6/2004 | Shillings et al. | |
| 2005/0273987 A1 | 12/2005 | Honchel | |
| 2006/0031988 A1 | 2/2006 | Morse | |
| 2007/0282272 A1 | 12/2007 | Bannon et al. | |
| 2011/0295210 A1* | 12/2011 | Wright | A61M 25/02 604/180 |
| 2012/0277682 A1 | 11/2012 | Corato et al. | |
| 2013/0165863 A1* | 6/2013 | Nilson | A61M 25/02 604/180 |
| 2014/0306070 A1 | 10/2014 | Hartsock et al. | |

FOREIGN PATENT DOCUMENTS

WO    WO2009110803    9/2009

\* cited by examiner

*Primary Examiner* — Todd M Epps

(57) ABSTRACT

A cable organizing assembly includes a pair of mounts. Each of the mounts includes a rotatable base. The rotatable base corresponding to each of the mounts may be removably coupled to a support. Each of the mounts includes a clamping unit. The clamping unit may engage at least one cable thereby facilitating the at least one cable to be removably coupled to the support.

11 Claims, 4 Drawing Sheets

CABLE ORGANIZING ASSEMBLY

BACKGROUND OF THE DISCLOSURE

Field of the Disclosure

The disclosure relates to organizing devices and more particularly pertains to a new organizing device for coupling at least one cable to a support.

SUMMARY OF THE DISCLOSURE

An embodiment of the disclosure meets the needs presented above by generally comprising a pair of mounts. Each of the mounts includes a rotatable base. The rotatable base corresponding to each of the mounts may be removably coupled to a support. Each of the mounts includes a clamping unit. The clamping unit may engage at least one cable thereby facilitating the at least one cable to be removably coupled to the support.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
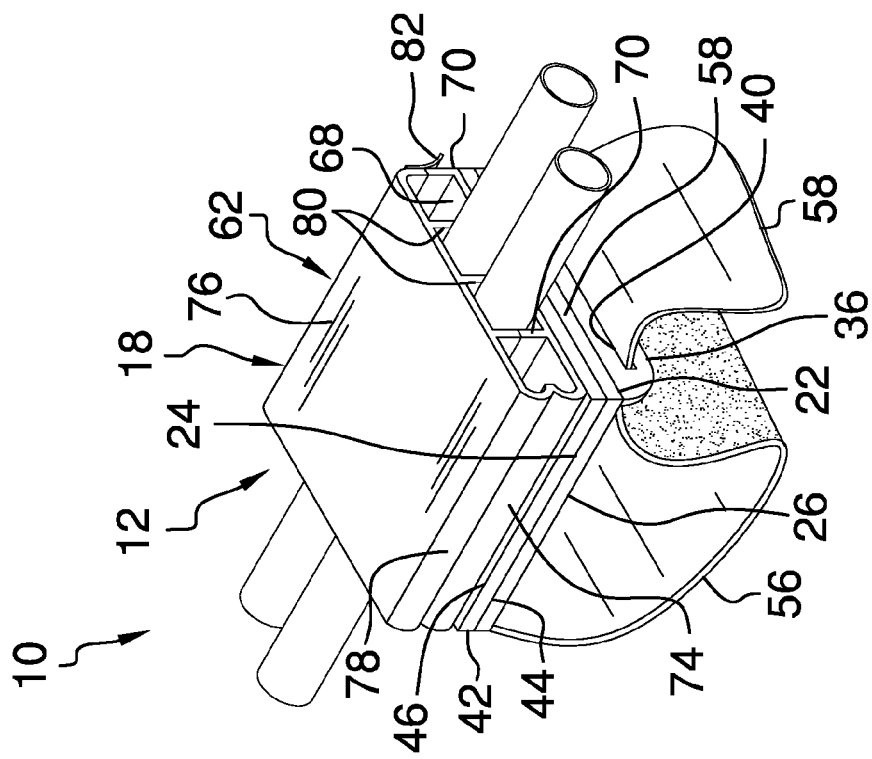
FIG. 1 is a top perspective view of a first mount of a cable organizing assembly according to an embodiment of the disclosure.
Figure 2:
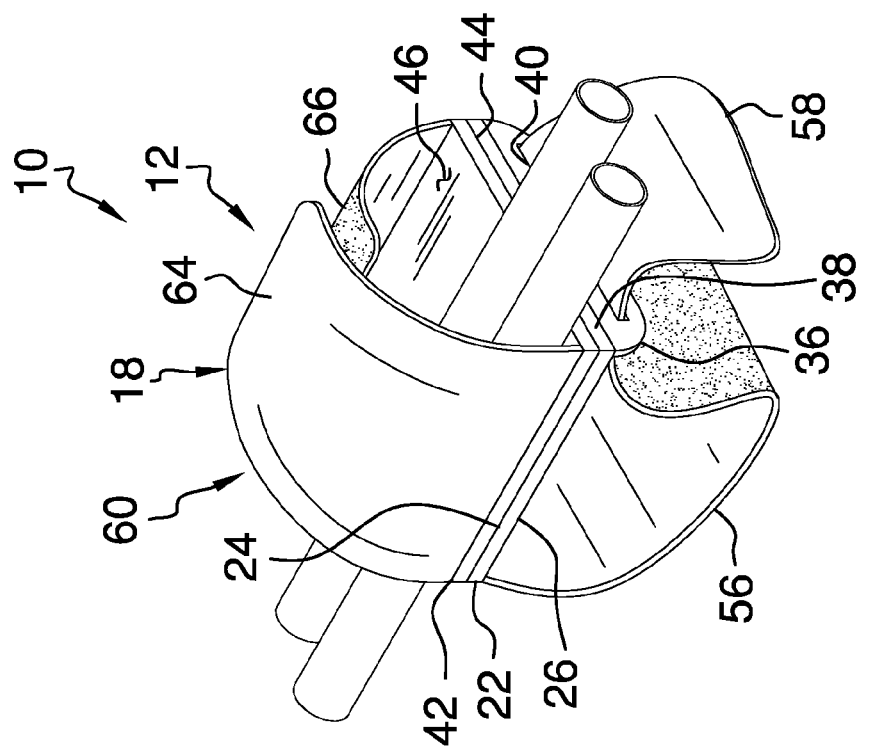
FIG. 2 is a top perspective view of a second mount of an embodiment of the disclosure.

With reference now to the drawings, and in particular to FIGS. 1 through 7 thereof, a new organizing device embodying the principles and concepts of an embodiment of the disclosure and generally designated by the reference numeral 10 will be described.

As best illustrated in FIGS. 1 through 7, the cable organizing assembly 10 generally comprises a pair of mounts 12. Each of the mounts 12 may be removably coupled to a support 14. The support 14 may comprise a rail on a hospital bed, a chair or other article of furniture. Each of the mounts 12 has a clamping unit 18 movably coupled thereto. The clamping unit 18 engages at least one cable 20. Thus, the at least one cable 20 may be removably coupled to the hospital bed 16. The at least one cable 20 may comprise an IV tube, an electrical cable or other cable commonly used in a medical environment.

Each of the mounts 12 comprises a first plate 22 that has a top surface 24 and a bottom surface 26. A rod 28 is coupled to and extends upwardly from the top surface 24. The rod 28 is centrally positioned on the first plate 22. The rod 28 has an outer surface 30 and the outer surface 30 has a plurality of indentations 32. Each of the indentations 32 extends toward a center of the rod 28. The indentations 32 are spaced apart from each other and are distributed around the rod 28.

The first plate 22 has a lip 36 extending downwardly from the bottom surface 26. The lip 36 is coextensive with a peripheral edge 38 of the first plate 22. The lip 36 has a slot 40 extending therethrough. The slot 40 is substantially coextensive with the lip 36.

A second plate 42 has a lower surface 44 and an upper surface 46. The lower surface 44 has a well 48 extending upwardly toward the upper surface 46 and the well 48 has a lateral bounding surface 50. The well 48 is centrally positioned on the second plate 42. The rod 28 extends into the well 48 such that the first plate 22 is rotatably coupled to the second plate 42. The rod 28 frictionally engages the lateral bounding surface 50 thereby retaining the rod 28 in the well 48.

A lock 52 is coupled to second plate 42. The lock 52 includes a ball 54 that is biased outwardly from the lock 52. The ball 54 may be biased via a spring biasing member or the like. The ball 54 extends outwardly from the lateral bounding surface 50 of the well 48. The ball 54 engages a selected one of the indentations 32 on the rod 28. Thus, the first plate 22 is movably retained at a selected angle of rotation with respect to the second plate 42.

A belt 56 is coupled to the bottom surface 26 of the first plate 22 and the belt 56 has a distal end 58 with respect to the bottom surface 26. The belt 56 may be wrapped around the support 14. The distal end 58 is extended through the slot 40 in the lip 36. The distal end 58 is matable to the belt 56 and the belt 56 may removably retain the first plate 22 on the support 14. The belt 56 may comprise a hook and loop fastener or the like.

The pair of mounts 12 includes a first mount 60 and a second mount 62. The clamping unit 18 corresponding to the first mount 60 includes a first strap 64. The first strap 64 is coupled to the second plate 42 corresponding to the first mount 60. A second strap 66 is coupled to the second plate 42 corresponding to the first mount 60. The first strap 64 is oppositionally positioned with respect to the second strap 66.

The first strap 64 is complementary with respect to the second strap 66. Each of the first strap 64 and the second strap 66 may be wrapped around the at least one cable 20. Thus, the at least one cable 20 may be removably coupled to the first mount 60. Each of the first strap 64 and the second strap 66 may comprise a hook and loop fastener of the like.

The clamping unit 18 corresponding to the second mount 62 comprises a first panel 68 that is coupled to the upper surface 46 corresponding to the second mount 62. The first panel 68 is coextensive with the upper surface 46 corresponding to the second mount 62. A plurality of medial walls 70 each extends upwardly from the first panel 68. The medial walls 70 are spaced apart from each other and are distributed along the first panel 68. Thus, a plurality of channels 72 is defined in the first panel 68. A selected one of the channels 72 may have the at least one cable 20 positioned therein. The first panel 68 has a first lateral edge 74.

A second panel 76 is provided and the second panel 76 has a first lateral edge 78. The first lateral edge 78 corresponding to the second panel 76 is hingedly coupled to the first lateral edge 74 corresponding to the first panel 68. A plurality of inner walls 80 each extends downwardly from the second panel 76. The inner walls 80 are spaced apart from each other and are distributed along the second panel 76.

Each of the inner walls 80 is aligned with an associated one of the medial walls 70. The second panel 76 is positionable in a closed position. Each of the inner walls 80 engages the associated medial wall 70. Thus, the second panel 76 may retain the at least one cable 20 in the selected channel 72.

A clip 82 is coupled to the second panel 76. The clip 82 engages the first panel 68 when the second panel 68 is positioned in the closed position. Thus, the second panel 68 is removably retained in the closed position.

Figure 3:
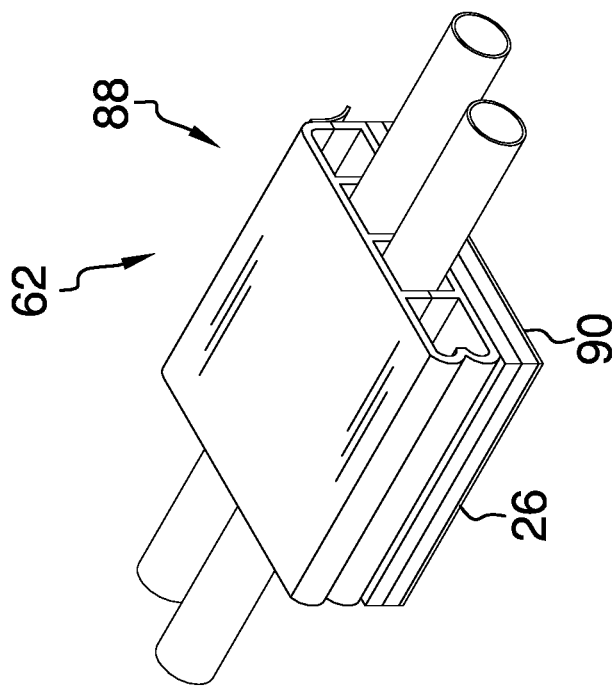
FIG. 3 is a front perspective view of first mount of an embodiment of the disclosure.
Figure 4:
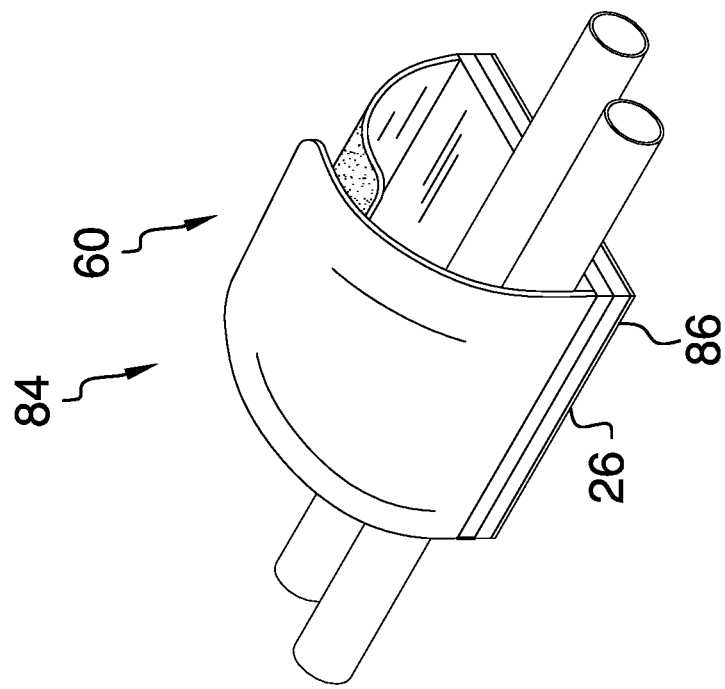
FIG. 4 is a front perspective view of a second mount of an embodiment of the disclosure.
Figure 6:
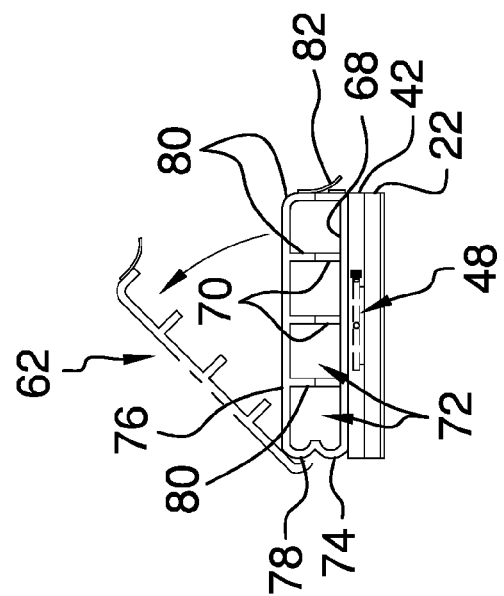
FIG. 6 is a front view of a second mount of an embodiment of the disclosure.
Figure 5:
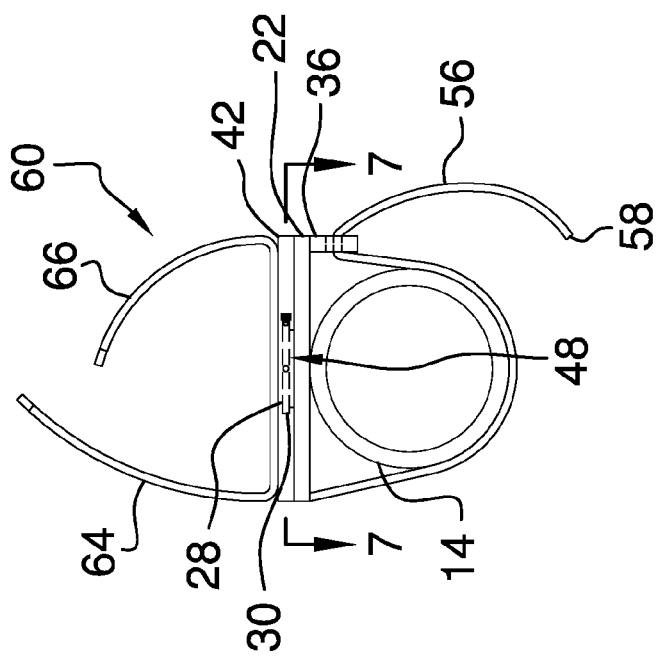
FIG. 5 is a front view of a first mount of an embodiment of the disclosure.
Figure 7:
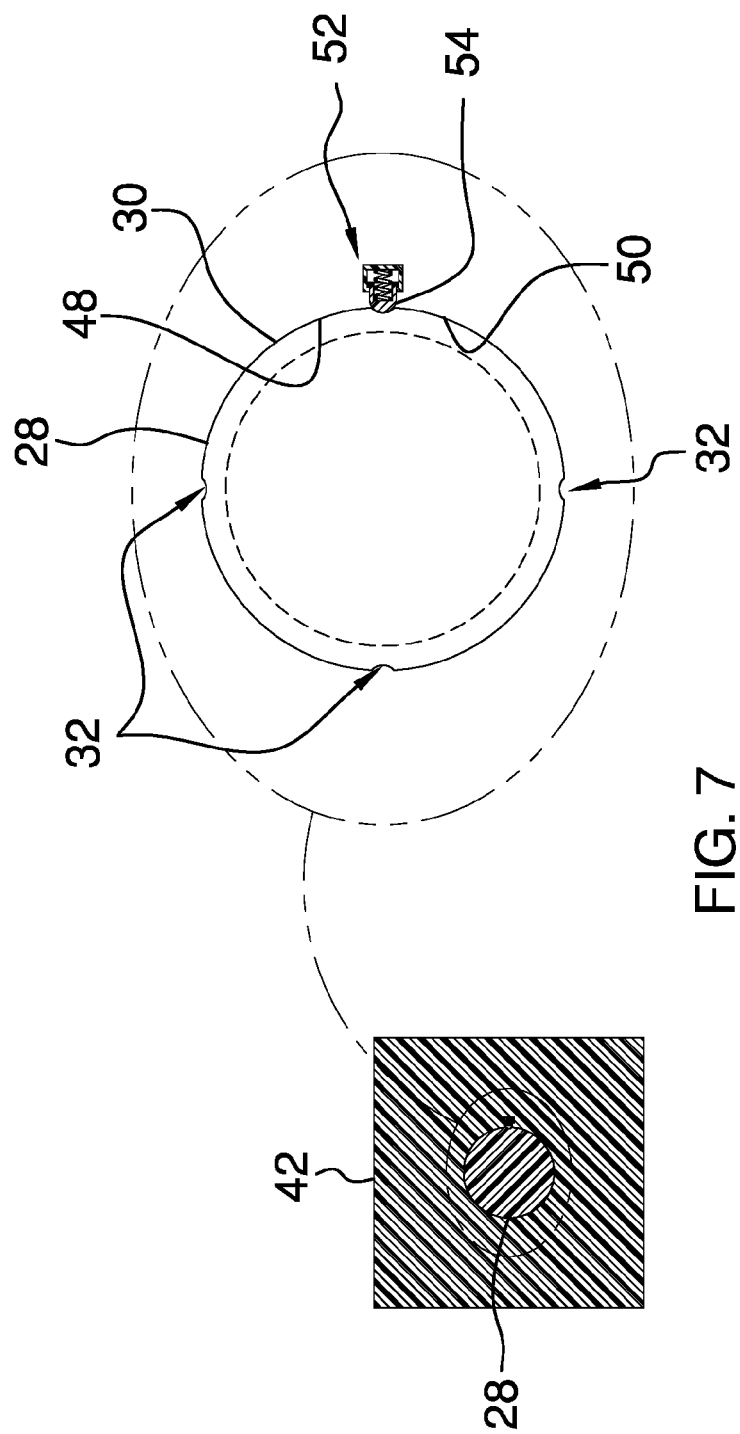
FIG. 7 is a cross sectional view taken along line 7-7 of FIG. 5 of an embodiment of the disclosure.

In an alternative embodiment 84 as shown in FIG. 3, an adhesive layer 86 may be coupled to the bottom surface 26 of the first mount 60. The adhesive layer 86 may adhesively engage the support 14. Thus, the first mount 60 may be coupled to the support 14. In an alternative embodiment 88 as shown in FIG. 4, an adhesive layer 90 may be coupled to the bottom surface 26 of the second mount 62. The adhesive layer 90 corresponding to the second mount 62 may adhesively engage the support 14. Thus, the second mount 62 may be coupled to the support 14.

In use, a selected one of the first mount 60 and the second mount 62 is coupled to the support 14. The selected first 60 and second 62 mount is positioned at a selected point on the support 14. The at least one cable 20 is placed on the upper surface 46 corresponding to the first mount 60. The first strap 64 is mated to the second strap 66 thereby retaining the at least one cable 20 on the first mount 60. The at least one cable 20 is placed in the selected channel 72 in the second mount 62. The second panel 76 is positioned in the closed position. Thus, the at least one cable 20 is retained on the second mount 62. Each of the first mount 60 and the second mount 62 inhibit the at least one cable 20 from becoming tangled or pulled free from a patient or associated medical equipment.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A cable organizing assembly comprising:
a pair of mounts, each of said mounts including a rotatable base, said rotatable base corresponding to each of said mounts being configured to be removably coupled to a support, each of said mounts having a clamping unit being movably coupled thereto, said clamping unit being configured to engage at least one cable thereby facilitating the at least one cable to be removably coupled to the support.

2. The assembly according to claim 1, wherein said rotatable base corresponding to each of said mounts comprises a first plate having a top surface and a bottom surface, said first plate having a rod being coupled to and extending upwardly from said top surface, said rod being centrally positioned on said first plate, said rod having an outer surface, said outer surface having a plurality of indentations, each of said indentations extending toward a center of said rod, said indentations being spaced apart from each other and being distributed around said rod.

3. The assembly according to claim 2, further comprising said first plate having a lip extending downwardly from said bottom surface, said lip being coextensive with a peripheral edge of said first plate, said lip having a slot extending therethrough.

4. The assembly according to claim 2, further comprising a second plate having a lower surface and an upper surface, said lower surface having a well extending upwardly toward said upper surface, said well having a lateral bounding surface, said well being centrally positioned on said second plate, said rod extending into said well such that said first plate is rotatably coupled to said second plate.

5. The assembly according to claim 4, further comprising a lock being coupled to said second plate, said lock having a ball being biased outwardly from said lock, said ball extending outwardly from said lateral bounding surface of said well, said ball engaging a selected one of said indentations on said rod such that said first plate is movably retained at a selected angle of rotation with respect to said second plate.

6. The assembly according to claim 3, further comprising a belt being coupled to said bottom surface of said first plate, said belt having a distal end with respect to said bottom surface, said belt being configured to be wrapped around the support, said distal end being extended through said slot in said lip, said distal end being matable to said belt wherein said belt is configured to removably retain said first plate on the support.

7. The assembly according to claim 1, wherein each of said pair of mounts includes a second plate, said pair of mounts including a first mount, said clamping unit corresponding to said first mount comprising:
a first strap being coupled to said second plate corresponding to said first mount; and
a second strap being coupled to said second plate corresponding to said first mount, said first strap being oppositionally positioned with respect to said second strap, said first strap being complementary with respect to said second strap, each of said first strap and said second strap being configured to be wrapped around the at least one cable thereby facilitating the at least one cable to be removably coupled to said first mount.

8. The assembly according to claim 1, wherein said pair of mounts includes a second mount, said clamping unit corresponding to said second mount comprising a first panel being coupled to an upper surface corresponding to said second mount, said first panel being coextensive with said upper surface corresponding to said second mount, said first panel having a plurality of medial walls each extending upwardly from said first panel, said medial walls being spaced apart from each other and being distributed along said first panel to define a plurality of channels in said first panel wherein a selected one of said channels is configured to have the at least one cable positioned therein, said first panel having a first lateral edge.

9. The assembly according to claim 8, further comprising a second panel having a first lateral edge, said first lateral edge corresponding to said second panel being hingedly coupled to said first lateral edge corresponding to said first panel, said second panel having a plurality of inner walls each extending downwardly from said second panel, said inner wall being spaced apart from each other and being distributed along said second panel, each of said inner walls being aligned with an associated one of said medial walls, said second panel being positionable in a closed position having each of said inner walls engaging said associated medial wall wherein said second panel is configured to retain the at least one cable in said selected channel.

10. The assembly according to claim 9, further comprising a clip being coupled to said second panel, said clip engaging said first panel when said second panel is positioned in said closed position such that said second panel is removably retained in said closed position.

11. A cable organizing assembly comprising:
   a pair of mounts, each of said mounts including a rotatable base, said rotatable base corresponding to each of said mounts being configured to be removably coupled to a support, each of said mounts having a clamping unit being movably coupled thereto, said clamping unit being configured to engage at least one cable thereby facilitating the at least one cable to be removably coupled to the support, said rotatable base corresponding to each of said mounts comprising:
      a first plate having a top surface and a bottom surface, said first plate having a rod being coupled to and extending upwardly from said top surface, said rod being centrally positioned on said first plate, said rod having an outer surface, said outer surface having a plurality of indentations, each of said indentations extending toward a center of said rod, said indentations being spaced apart from each other and being distributed around said rod, said first plate having a lip extending downwardly from said bottom surface, said lip being coextensive with a peripheral edge of said first plate, said lip having a slot extending therethrough,
      a second plate having a lower surface and an upper surface, said lower surface having a well extending upwardly toward said upper surface, said well having a lateral bounding surface, said well being centrally positioned on said second plate, said rod extending into said well such that said first plate is rotatably coupled to said second plate,
      a lock being coupled to second plate, said lock having a ball being biased outwardly from said lock, said ball extending outwardly from said lateral bounding surface of said well, said ball engaging a selected one of said indentations on said rod such that said first plate is movably retained at a selected angle of rotation with respect to said second plate, and
      a belt being coupled to said bottom surface of said first plate, said belt having a distal end with respect to said bottom surface, said belt being configured to be wrapped around the support, said distal end being extended through said slot in said lip, said distal end being matable to said belt wherein said belt is configured to removably retain said first plate on the support;
   said pair of mounts comprising a first mount and a second mount, said clamping unit corresponding to said first mount comprising:
      a first strap being coupled to said second plate corresponding to said first mount, and
      a second strap being coupled to said second plate corresponding to said first mount, said first strap being oppositionally positioned with respect to said second strap, said first strap being complementary with respect to said second strap, each of said first strap and said second strap being configured to be wrapped around the at least one cable thereby facilitating the at least one cable to be removably coupled to said first mount; and
   said clamping unit corresponding to said second mount comprising:
      a first panel being coupled to said upper surface corresponding to said second mount, said first panel being coextensive with said upper surface corresponding to said second mount, said first panel having a plurality of medial walls each extending upwardly from said first panel, said medial walls being spaced apart from each other and being distributed along said first panel to define a plurality of channels in said first panel wherein a selected one of said channels is configured to have the at least one cable positioned therein, said first panel having a first lateral edge,
      a second panel having a first lateral edge, said first lateral edge corresponding to said second panel being hingedly coupled to said first lateral edge corresponding to said first panel, said second panel having a plurality of inner walls each extending downwardly from said second panel, said inner wall being spaced apart from each other and being distributed along said second panel, each of said inner walls being aligned with an associated one of said medial walls, said second panel being positionable in a closed position having each of said inner walls engaging said associated medial wall wherein said second panel is configured to retain the at least one cable in said selected channel, and
      a clip being coupled to said second panel, said clip engaging said first panel when said second panel is positioned in said closed position such that said second panel is removably retained in said closed position.

\* \* \* \* \*